(12) United States Patent
Burry et al.

(10) Patent No.: US 8,506,942 B2
(45) Date of Patent: Aug. 13, 2013

(54) HAIR CARE COMPOSITION

(75) Inventors: Jason Shaun Burry, Wirral (GB);
Richard Livesey Evans, Wirral (GB);
Graham Andrew Turner, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 271 days.

(21) Appl. No.: 12/739,159

(22) PCT Filed: Oct. 23, 2008

(86) PCT No.: PCT/EP2008/064360
§ 371 (c)(1),
(2), (4) Date: Sep. 17, 2010

(87) PCT Pub. No.: WO2009/053431
PCT Pub. Date: Apr. 30, 2009

(65) Prior Publication Data
US 2011/0003016 A1    Jan. 6, 2011

(30) Foreign Application Priority Data

Oct. 25, 2007 (EP) .................................. 07119286

(51) Int. Cl.
*A61Q 5/00* (2006.01)
(52) U.S. Cl.
USPC .......................................... 424/74; 424/70.1
(58) Field of Classification Search
None
See application file for complete search history.

(56) References Cited

U.S. PATENT DOCUMENTS

| 604,111 | A | 5/1898 | Edwards | |
| 6,232,302 | B1 | 5/2001 | Alberico et al. | 514/54 |
| 2007/0036742 | A1 | 2/2007 | Roufs et al. | 424/74 |
| 2009/0123536 | A1 | 5/2009 | Castan et al. | |

FOREIGN PATENT DOCUMENTS

| DE | 102005010142 A1 | 11/2005 |
| DE | 102005010142-TR A1 | 11/2005 |
| EP | 1089704 B1 | 11/2004 |
| EP | 1 700 617 | 9/2006 |
| EP | 1700 617 * | 9/2006 |
| EP | 1800 715 * | 6/2007 |
| WO | WO9631188 | 10/1996 |
| WO | 99/30675 | 6/1999 |
| WO | 99/66887 | 12/1999 |
| WO | 0048559 | 8/2000 |
| WO | 2006087394 A1 | 8/2006 |

OTHER PUBLICATIONS

Paus et al., Journal of Dermatological Science, Correlation of proteolytic activites of organ cultured intact mouse skin with defined hair cycle stages, vol. 7, 1994, pp. 202-209.
Schwarzenberger et al., Journal of Investigative Dermatology, Contact Allergens and Epidermal Proinflammatory Cytokines Modulate Langerhans Cell E-cadherin Expression in Situ, vol. 106, No. 3, 1996, pp. 553-558.
PCT International Search Report in PCT application PCT/EP2008/064360.
European Search Report in EP application EP 07 11 9286.
Abstract of EP 1 700 617—published Sep. 13, 2006.
Freis et al., "*Hair care active ingredients—Cosmetic properties and methods for evaluating their efficacy*", Skin Care Forum, vol. 27, November, 1001, pp. 1-10.
English translation of opposition letter from Henkel to EPO, Munich, dated Nov. 5, 2012.
Product data sheet for raw material Trichogen(R) VEG LS 8960; pp. 1-3, dated Jun. 2007.
BASF The Chemical Company; "Hair care active ingredients—cosmetic properties and methods for evaluation their efficacy"; Nov. 2001; pp. 1-8.
Hoechst data sheet for piroctone olamine; Aug. 23, 1983 with translation of same.
Mintel, Anti-Dandruff Shampoo printout; Oct. 2005, pp. 1-2.
Mintel, Shampoo Dense printout; Jul. 2005, pp. 1-2.
Mintel, Shampoo Repair printout; Jul. 2005, pp. 1-2.
Mintel, Anti-Dandruff Shampoo printout; Aug. 2006, pp. 1-2.
Mintel, Anti-Dandruff Shampoo with Ginsena printout; Mar. 2006, pp. 1-2.
Mintel, Anti-Dandruff Multi-V Shampoo printout; Jan. 2002, pp. 1-2.

\* cited by examiner

*Primary Examiner* — Jyothsna Venkat
(74) *Attorney, Agent, or Firm* — Ronald A. Koatz

(57) ABSTRACT

A hair treatment composition comprising a trichogenic material and an anti-dandruff agent.

2 Claims, No Drawings

HAIR CARE COMPOSITION

The present invention relates to hair care compositions in particular compositions that maximize hair growth.

Hair growth is of commercial interest to many groups of consumer. Male baldness or hair thinning is a problem for one market segment, a second market segment is people who are not bald but require their hair to appear thick and voluminous. For male baldness the predominant products are pharmaceuticals, although not all the products that are marketed in this segment are drug products.

The prior art includes many patents disclosing hair grooming compositions which illustrate the state of the art in herbal based compositions for promoting hair health and growth.

U.S. Pat. No. 604,111 discloses a hair tonic of mountain sage, glycerin, tincture of lobella, prickly pear juice, tincture of capsicum, sweet oil, and alcohol, which cleans the scalp, relaxes and stimulates the scalp, cools the scalp and gives the hair gloss.

US 2007/0036742 discloses a composition for preventing or decreasing hair loss comprising a mixture of plant extracts such as green tea.

U.S. Pat. No. 6,232,302 discloses compositions comprising depolymerises fucane sulphates for increasing hair growth.

Compositions comprising cysteine, lysine, and a glycoprotein are disclosed in EP 1 089 704 for trichological use.

The present invention concerns the problem of poor hair thickness, poor hair growth and hair shedding and discloses compositions that mitigate these problems.

The present invention relates to a hair treatment composition a hair treatment composition comprising a trichogenic material and an anti-dandruff agent.

The composition of the invention comprises a trichogenic material. Preferably the trichogenic material comprises a synergistic trichogenic mixture of the following: a protein biosynthesis stimulant preferably selected from a sulfopeptide of soy, amino acids, glutamine, glutamic acid, hydrolysed protein extracts, particularly preferred are sulfopeptides of soy and amino acids, especially tyrosine, arginine, ornithine and citrulline.

The synergistic trichogenic mixture may comprise a glycosamino production agent is selected from the group consisting of glucosamine, L-fucose; fucose rich polysaccharide, xylose, vitamin C, *Eriobotrya japonica* extract, N-acetyl glucosamine, glucosamine sulphate, lysophospholipids, protamine and mixtures thereof. Particularly preferred is glucosamine.

The synergistic trichogenic mixture may comprise a cell nutrition regulator especially vitamins of the B group, carnitine, co-enzyme Q10, creatine, taurine, acetyl-carnitine and mixtures thereof. Particularly preferred are vitamins of the B group, especially PP, B5 and biotin.

The synergistic trichogenic mixture may comprise a microcirculation promoter, preferred promoters are *Panax Ginseng* Extract, *Arctium Majus* Extract, nitric oxide, niacin, caffeine, gingko biloba extract, bicyclic monoterpene diols, α-lipoic acid, ximenynic acid, proanthocyanidins, arginine and mixtures thereof. Particularly preferred are *Panax Ginseng* Extract, *Arctium Majus* Extract.

It is preferred if the mixture comprise at least one ingredient from the above listed groups of actives that is at least one healthy scalp protein biosynthesis stimulant, at least one glycosamino production agent, at least one cell nutrition regulator and at least one microcirculation promoter. A particularly preferred synergistic trichogenic mixture is known as Trichogen® ex Cognis, in particular Trichogen® Veg LS 8960.

The level of the synergistic trichogenic mixture is preferably from 0.001 to 20 wt % of the total composition, more preferably from 0.1 to 15 wt % of the total composition, most preferably from 0.2 t 10 wt % of the total composition.

The antidandruff agent is selected form the group consisting of zinc pyrithione, octopirox, climbazole, ketoconazole and mixtures thereof. Azole based antidandruff agents are preferred, in particular climbazole.

The anti-dandruff agent is therefore preferably soluble in the composition of the invention at 25° C.

The level of anti-dandruff is preferably from 0.005 to 5 wt %, more preferably from 0.01 to 3 wt % of the total composition.

Preferably the ratio of trichogenic material to anti-dandruff material is from 1:1 to 100:1, more preferably from 2:1 to 50:1, most preferably from 5:1 to 30:1.

It is preferable if the composition of the invention further comprises an anti-inflammatory agent. Preferably the anti-inflammatory agent is selected form the group consisting of hyssop extract, turmeric extract, arnica extract, willow bark extract, sesquiterpene extract, salicylic acid and mixtures thereof. An especially preferred anti-inflammatory agent is salicylic acid.

The final product form of hair treatment compositions according to the invention may suitably be, for example, shampoos, conditioners, sprays, mousses, gels, oils, creams, waxes or lotions. Particularly preferred product forms are leave-on products (those products that are not immediately rinsed off after application and are preferably left on for at least one hour, more preferably for at least 5 hours). Post-wash conditioners are preferred (especially leave-in) as are hair treatment products such as hair essences.

The amount of product applied will vary according to the form of the product, but will normally be in accordance with the industry accepted methodology for the use of a product of the same type. A representative application procedure will involve application of the formulation to the area in need of treatment once or twice a day, and leaving the formulation in place for a period of several hours.

Conditioner compositions usually comprise one or more conditioning surfactants, which are cosmetically acceptable and suitable for topical application to the hair.

Suitable conditioning surfactants are selected from cationic surfactants, used singly or in a mixture.

Cationic surfactants useful in compositions of the invention contain amino or quaternary ammonium hydrophilic moieties, which are positively charged when, dissolved in the aqueous composition of the present invention.

The most preferred cationic surfactants for conditioner compositions of the present invention are monoalkyl quaternary ammonium compounds in which the alkyl chain length is $C_{16}$ to $C_{22}$.

Examples of suitable cationic surfactants include quaternary ammonium compounds, particularly trimethyl quaternary compounds.

Preferred quaternary ammonium compounds include cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as Genamin® CTAC, ex Clariant.

Salts of primary, secondary, and tertiary fatty amines are also suitable cationic surfactants.

In the conditioners of the invention, the level of cationic surfactant is preferably from 0.01 to 10, more preferably 0.05 to 5, most preferably 0.1 to 2 wt % of the total composition.

Conditioner compositions of the invention preferably additionally comprise fatty materials. By "fatty material" is meant a fatty alcohol, an alkoxylated fatty alcohol, a fatty acid, a glyceride, glycerol, plant unsaponifiables or a mixture thereof.

Or propoxylated fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 wt %. The weight ratio of cationic surfactant to fatty alcohol is suitably from 10:1 to 1:10, preferably from 4:1 to 1:8, optimally from 1:1 to 1:7, for example 1:3.

In a preferred embodiment, the hair treatment composition, especially if it is a shampoo composition, further comprises from 0.1 to 5 wt % of a suspending agent.

The compositions of the invention can contain emulsified droplets of a silicone-conditioning agent, for enhancing conditioning performance.

Suitable silicones include polydiorganosiloxanes, in particular polydimethylsiloxanes which have the CTFA designation dimethicone. Also suitable for use in compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

A further preferred class of silicones for inclusion in shampoos and conditioners of the invention are amino function.

The total amount of silicone is preferably from 0.01 to 10% wt of the total composition more preferably from 0.3 to 5, most preferably 0.5 to 3 wt % is a suitable level.

Compositions according to the present invention may also comprise a dispersed, non-volatile, water-insoluble oily conditioning agent.

By "insoluble" is meant that the material is not soluble in water (distilled or equivalent) at a concentration of 0.1% (w/w), at 25° C.

Suitable oily or fatty materials are selected from hydrocarbon oils, fatty esters and mixtures thereof.

The compositions of the present invention may also contain adjuvants suitable for hair care. Generally such ingredients are included individually at a level of up to 2, preferably up to 1 wt % of the total composition.

Suitable hair care adjuvants include amino acids, sugars and ceramides.

Styling Polymers

The hair styling polymer if present is preferably present in the compositions of the invention in an amount of from 0.001% to 10% by weight, more preferably from 0.1% to 10% by weight, such as from 1% to 8% by weight.

Hair styling polymers are well known. Suitable hair styling polymers include commercially available polymers that contain moieties that render the polymers cationic, anionic, amphoteric or nonionic in nature. Suitable hair styling polymers include, for example, block and graft copolymers. The polymers may be synthetic or naturally derived.

Shampoo compositions preferably comprise one or more cleansing surfactants, which are cosmetically acceptable and suitable for topical application to the hair. Further surfactants may be present as emulsifiers.

Suitable cleansing surfactants are selected from anionic, amphoteric and zwitterionic surfactants and mixtures thereof. The cleansing surfactant may be the same surfactant as the emulsifier, or may be different.

Shampoo compositions according to the invention will typically comprise one or more anionic cleansing surfactants, which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. Typical anionic cleansing surfactants for use in shampoo compositions of the invention include sodium oleyl sulpho succinate, ammonium lauryl sulphosuccinate, ammonium lauryl sulphate, sodium cocoyl isethionate, sodium lauryl isethionate and sodium N-lauryl sarcosinate. The most preferred anionic surfactants are sodium lauryl sulphate, sodium lauryl ether sulphate (n)EO, (where n ranges from 1 to 3), ammonium lauryl sulphate and ammonium lauryl ether sulphate(n)EO, (where n ranges from 1 to 3).

The total amount of anionic cleansing surfactant in shampoo compositions of the invention is generally from 5 to 30, preferably from 6 to 20, more preferably from 8 to 16 wt %.

The shampoo composition can optionally include co-surfactants, preferably an amphoteric or zwitterionic surfactant, which can be included in an amount ranging from 0 to 8, preferably from 1 to 4 wt %.

Examples of amphoteric and zwitterionic surfactants include, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred co-surfactant is a nonionic surfactant, which can be included in an amount ranging from 0 to 8, preferably from 2 to 5 wt %.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain $C_5$ to $C_{20}$ alkyl or alkenyl group, G is a saccharide group and n is from 1 to 10.

The shampoo composition can also optionally include one or more cationic co-surfactants included in an amount ranging from 0.01 to 10, more preferably from 0.05 to 5, most preferably from 0.05 to 2 wt %. Useful cationic surfactants are described below in relation to conditioner compositions.

The total amount of surfactant (including any co-surfactant, and/or any emulsifier) in shampoo compositions of the invention is generally from 5 to 50, preferably from 5 to 30, more preferably from 10 to 25 wt %.

A cationic polymer is a preferred ingredient in compositions of the invention, for enhancing conditioning performance of the shampoo.

Suitable cationic nitrogen polymers are described in the CTFA Cosmetic Ingredient Directory, 3rd edition.

The cationic conditioning polymer will generally be present in compositions of the invention at levels of from 0.01 to 5, preferably from 0.05 to 1, more preferably from 0.08 to 0.5 wt %.

The invention is further illustrated by the following non-limiting examples:

EXAMPLES

Hair growth follows a cycle of activity: anagen (growth phase), catagen (transitional/regression phase), telogen (dormant) followed by renewal of anagen. The telogen phase lasts approximately 3 months. As this phase progresses the strength of anchoring the hair fibre in the follicle is gradually reduced, eventually resulting in hair loss (the exogen phase). The major biochemical activity at this stage is one of proteolysis whereby the proteins anchoring the hair fibre to the structure of the follicle are degraded (Paus & Krejic-Papa J Dermatol Sci 1994 Vol. 7, pp. 202-209; Krejic-Papa et al J Invest Derm Vol. 106, p 557). These enzymes are of the serine protease family of proteases.

Trypsin is a serine protease.

The following experiment uses trypsin as a model for the serine proteases involved in the process of hair fall (exogen). Successful inhibition the activity of the serine proteases such as trypsin is thought to delay the onset of exogen and decrease the amount of hair fall.

The EnzChek Protease Assay (E6639, Molecular Probes) was used to measure trypsin activity.

Examples of Synergy with Climbazole and Trichogen (Trypsin Inhibition)

Example 1

| Ingredient | Trypsin activity (RFU) | Normalised activity |
|---|---|---|
| Control (Trypsin only) | 1446 | 1.0 |
| a. Climbazole (0.045%) | 1553 | 1.07 |
| b. Trichogen (1.25%) | 826 | 0.57 |
| Calculated (a + b) | — | 0.64 |
| Experimental (a + b) | 500 | 0.35 |

Example 2

| Ingredient | Trypsin activity (RFU) | Normalised activity |
|---|---|---|
| Control (Trypsin only) | 1446 | 1.0 |
| a. Climbazole (0.045%) | 1553 | 1.07 |
| c. Trichogen (0.63%) | 768 | 0.53 |
| Calculated (a + c) | — | 0.60 |
| Experimental (a + c) | 429 | 0.30 |

Example 3

| Ingredient | Trypsin activity (RFU) | Normalised activity |
|---|---|---|
| Control (Trypsin only) | 1446 | 1.0 |
| a. Climbazole (0.045%) | 1553 | 1.07 |
| d. Trichogen (0.31%) | 766 | 0.53 |
| Calculated (a + d) | — | 0.60 |
| Experimental (a + d) | 384 | 0.27 |

Example 4

| Ingredient | Trypsin activity (RFU) | Normalised activity |
|---|---|---|
| Control (Trypsin only) | 1446 | 1.0 |
| e. Climbazole (0.0225%) | 1656 | 1.15 |
| b. Trichogen (1.25%) | 826 | 0.57 |
| Calculated (e + b) | — | 0.72 |
| Experimental (e + b) | 702 | 0.49 |

Example 5

| Ingredient | Trypsin activity (RFU) | Normalised activity |
|---|---|---|
| Control (Trypsin only) | 1446 | 1.0 |
| e. Climbazole (0.0225%) | 1656 | 1.15 |
| c. Trichogen (0.63%) | 768 | 0.53 |
| Calculated (e + c) | — | 0.68 |
| Experimental (e + c) | 716 | 0.50 |

Example 6

| Ingredient | Trypsin activity (RFU) | Normalised activity |
|---|---|---|
| Control (Trypsin only) | 1446 | 1.0 |
| e. Climbazole (0.0225%) | 1656 | 1.15 |
| d. Trichogen (0.31%) | 766 | 0.53 |
| Calculated (e + d) | — | 0.68 |
| Experimental (e + d) | 757 | 0.52 |

The above tables show that climbazole has no effect (or perhaps a positive effect) on trypsin activity. Trichogen® has an inhibitory effect on trypsin activity. Surprisingly the combination of trichogen and climbazole provided a synergistic inhibition of the enzyme.

To further support this work a clinical study was undertaken. In this study a 7 ml solution of 5 wt % Trichogen® and 0.5 wt % climbazole was applied to the hair after washing and conditioning every second day. It was left on the scalp during drying/styling. The study showed that a significant decrease in hair fall was achieved after 12 and 16 weeks of treatment.

| Shampoo | | | | | |
|---|---|---|---|---|---|
| Climbazole | 2.00 | 2.00 | 1.00 | 1.00 | — |
| Zn PTO | | | | | 1.0 |
| Ethanol | 5.0 | 5.0 | 5.0 | 5.0 | 5.0 |
| Salicylic acid | — | 1.0 | — | 1.0 | |
| Trichogen Veg | 10.00 | 10.00 | 10.00 | 5.00 | 5.00 |
| Sodium Laureth Sulfate | 7.70 | 7.70 | 7.70 | 7.70 | 7.70 |
| Disodium Laureth Sulfosuccinate | 12.50 | 12.50 | 12.50 | 12.50 | 12.50 |
| Cocamidopropyl Betaine | 9.60 | 9.60 | 9.60 | 9.60 | 9.60 |
| Guar Hydroxypropyltrimonium Chloride | 0.20 | 0.20 | 0.20 | 0.20 | 0.20 |
| DMDM Hydantoin | 0.10 | 0.10 | 0.10 | 0.10 | 0.10 |
| Tetrasodium EDTA | 0.20 | 0.20 | 0.20 | 0.20 | 0.20 |
| Water and minors | To 100 wt % | | | | |

| Conditioner: | | |
|---|---|---|
| Lexamine S13 | 1.25 | 1.25 |
| Ganamin BTLF | 1.25 | 1.25 |
| Laurex CS | 5.00 | 5.00 |
| Potassium Chloride | 0.10 | 0.10 |
| EDTA | 0.10 | 0.10 |
| DMDM Hydantoin | 0.10 | 0.10 |
| Lauric Acid | 0.30 | 0.30 |
| Trichogen Veg | 5.0 | 10.0 |
| Climbazole | 0.50 | — |
| ZnPTO | — | 1.00 |
| Water and Minors | To 100% | To 100% |

Lexamine S13 (ex Inolex Chemical Company is Stearamidopropyl Dimethylamine
Ganamin BTLF (ex Clariant) is Behentrimonium Chloride
Laurex CS (ex Abright and Wilson) is Cetearyl Alcohol

| Leave-on serum | | |
|---|---|---|
| Ingredient | | |
| Water + minors | To 100% | To 100% |
| Carbopol Ultrez 20 | 0.40 | 0.40 |
| Propylene Glycol | 4.00 | 4.00 |
| Glycerol | 2.00 | 2.00 |
| Rhodasurf L790 | 1.11 | 1.11 |
| Eumulgin L | 3.00 | 3.00 |
| DC245 | 0.50 | 0.50 |
| Fragrance | 0.50 | 0.50 |
| Trichogen VEG | 5.00 | 10.00 |
| Climbazole | 0.50 | 0.50 |
| Ethanol | 5.00 | 5.00 |

Carbopol Ultrez 20 (ex Noveon) is a hydrophobically modified cross-linked acrylate copolymer (Acrylates/C10-30 Alkyl Acrylate Crosspolymer)
Rhodasurf L790 (ex Rhodia) is polyoxyethylene 7 lauryl alcohol (Laurette-7)
Eumulgin L (ex Cognis) is PPG-1-PEG-9 Lauryl Glycol Ether

The invention claimed is:

1. A hair treatment composition consisting of
    (a) 0.1% to 20% of wt. of a trichogenic material
        wherein the tricohogenic material is a mixture of water, panax ginseng root extract, arginine, acetyl tyrosine, arctium majus root extract, hydrolyzed soy protein, polyquaternium 11, PEG-12 dimethicone, calcium pantothenate, zinc gluconate, niacinamide, orthinine hydrochloride, citrulline, glucosamine hydrochloride and biotin
    (b) 0.05% to 5% by wt. of an antidandruff agent selected from the group consisting of zinc pyrithione, octopirox, climbazole, ketoconazole and mixtures thereof
    (c) 5% to 50% by weight of surfactant
    (d) 0.01% to 15% by weight of fatty alcohol
    (e) 0.1% to 5% by weight of suspending agent
    (f) 0.01% to 10% by weight of silicone
    (g) up to 2% of adjuvant and the remaining water.

2. A hair treatment composition according to claim 1 wherein the antidandruff agent is climbazole.

\* \* \* \* \*